(12) United States Patent
Fischler et al.

(10) Patent No.: US 8,944,817 B2
(45) Date of Patent: Feb. 3, 2015

(54) CONNECTION OF A PROSTHESIS STRUCTURE WITH AN IMPLANT STRUCTURE

(75) Inventors: Titus Fischler, Zeiningen (CH); Elisabeth Fischler, Zeiningen (CH); Martin Bächler, Seltisberg (CH); Jürg Bächler, Hölstein (CH); Roland Schaffner, Liestal (CH)

(73) Assignees: Jurg Bachler, Holstein (CH); Martin Bachler, Oberdorf (CH)

( * ) Notice: Subject to any disclaimer, the term of this patent is extended or adjusted under 35 U.S.C. 154(b) by 0 days.

(21) Appl. No.: 13/807,807

(22) PCT Filed: Dec. 28, 2010

(86) PCT No.: PCT/IB2010/003380
§ 371 (c)(1),
(2), (4) Date: Dec. 31, 2012

(87) PCT Pub. No.: WO2011/027229
PCT Pub. Date: Mar. 10, 2011

(65) Prior Publication Data
US 2013/0101960 A1      Apr. 25, 2013

(30) Foreign Application Priority Data
Jul. 2, 2010   (EP) .................................... 10168364

(51) Int. Cl.
*A61C 13/10*   (2006.01)
*A61C 8/00*   (2006.01)
*A61C 13/265*   (2006.01)
*A61C 5/08*   (2006.01)

(52) U.S. Cl.
CPC ............... *A61C 8/005* (2013.01); *A61C 8/0048* (2013.01); *A61C 8/0089* (2013.01); *A61C 13/2656* (2013.01); *A61C 5/08* (2013.01); *A61C 8/0016* (2013.01); *A61C 8/0062* (2013.01)
USPC ........................... 433/177; 433/173; 433/191

(58) Field of Classification Search
CPC ............. A61C 13/265; A61C 13/2653; A61C 13/2656; A61C 8/005; A61C 8/0053; A61C 8/0069
USPC ............... 433/172–176, 177–178, 201.1, 191
See application file for complete search history.

(56) References Cited

U.S. PATENT DOCUMENTS 4,362,509 A * 12/1982 Sulc ............................. 433/181
5,417,570 A * 5/1995 Zuest et al. ................... 433/177

(Continued)

FOREIGN PATENT DOCUMENTS

EP    0 891 750 A1    1/1999

OTHER PUBLICATIONS

International Search Report for International Application No. PCT/IB2010/003380 dated Aug. 12, 2011.

*Primary Examiner* — Edward Moran
(74) *Attorney, Agent, or Firm* — Kratz, Quintos & Hanson, LLP

(57) ABSTRACT

A connection device includes a holding shell and a retention insert. The retention insert has an end side and a substantially ring-shaped retention rim projecting therefrom. The holding shell has an end side and a substantially ring-shaped holding rim projecting therefrom. An outer surface of the retention rim is at least partly spaced from and adjacent to an inner surface of the holding rim when the retention insert is arranged in the holding shell and when essentially no radial forces are acting on the holding rim and on the retention rim. In that the outer surface of the retention rim and inner surface of the holding rim are at least partly not contacting each other when essentially no radial forces are acting, it can be achieved that the retention insert is connected relatively loosely with the holding shell when the connection device has not yet been placed on the implant structure.

10 Claims, 7 Drawing Sheets

(56) References Cited

U.S. PATENT DOCUMENTS

| | | | |
|---|---|---|---|
| 6,190,169 B1* | 2/2001 | Bluemli et al. | 433/172 |
| 6,981,871 B2* | 1/2006 | Mullaly et al. | 433/172 |
| 8,317,515 B2* | 11/2012 | Seo et al. | 433/173 |
| 2006/0160048 A1* | 7/2006 | Honkura et al. | 433/189 |
| 2009/0130629 A1* | 5/2009 | Towse et al. | 433/174 |
| 2010/0055645 A1 | 3/2010 | Mullaly | |

* cited by examiner

CONNECTION OF A PROSTHESIS STRUCTURE WITH AN IMPLANT STRUCTURE

TECHNICAL FIELD

The invention relates to a connection device as well to a corresponding retention insert, a corresponding method and a corresponding mounting tool. Connection devices of this kind, which comprise a holding shell and a retention insert, wherein the holding shell has an end side and a substantially ring-shaped holding rim projecting therefrom and the retention insert has an end side and a substantially ring-shaped retention rim projecting therefrom, and wherein the holding rim and the end side of the holding shell form a retainer in which the retention insert can be arranged such that an outer surface of the retention rim of the retention insert is located adjacent to an inner surface of the holding rim of the holding shell, can be used for connecting a dental prosthesis structure with a dental implant structure or with a capped tooth.

PRIOR ART

In dentistry, damaged or diseased teeth are nowadays regularly replaced with artificial dentures. Such dentures can be configured in various ways for a single tooth, a plurality of teeth together or as full dentures.

Such a denture often comprises an implant structure and a prosthesis structure. The prosthesis structure can comprise a synthetic prosthesis material as carrier material and one or more tooth crowns attached thereto. The implant structure can be formed as one part or also consist of more parts, wherein two-part structures typically comprise a dental implant and a connector or abutment, respectively. Moreover, the implant structure can also comprise a web which is connected across several dental implants with the jaw bone. The dental implant or the entire implant structure is engrafted as an artificial root of the tooth at a target place in a jaw bone of a patient. To this end, the jaw bone is partially treated in advance in that, for example, bone substance is built (osseosynthesis) or replaced with artificial tissue and/or in that a drill hole is provided at the target place in the jaw bone. Then, the dental implant or the implant structure is generally screwed into the jaw bone, for example via a screw thread, as an enossal dental implant or it is just put into it. Within typically three to six months, the dental implant or the implant structure and the surrounding jaw bone unite to form a tight and strong carrier unit. This process is referred to as osseointegration. Dental implants or implant structures are typically made of titanium or also of ceramic materials. If it is possible, alternatively to dental implants, also capped teeth are connected with prosthesis structures, wherein to this end a cap is attached to the tooth or a remainder of a tooth. In the following, capped teeth are not mentioned separately to simplify matters, but they can also be used as an alternative to the mentioned implant structures.

Nowadays a plurality of different connection mechanisms are used for mounting the prosthesis structure to the engrafted implant structure. For a comfortable releasable connection, in particular snap-engagement structures are used, wherein the implant structure comprises a female or male part and the prosthesis structure comprises a corresponding male or female part. For example, WO 2010/025034 A1 describes a snap-engagement system as such a connection mechanism. Thereby, the implant structure is formed, e.g., as one part and comprises a head having a flat end and an adjoining portion being bulged outwardly. Moreover, a holder being open in the direction of the flat end is provided in the center of the head. The prosthesis structure comprises a retention part made of a synthetic material and a cap made of titanium. The retention part is substantially cup-shaped, wherein the inner side of its rim is formed in accordance with the bulged portion of the head of the implant structure. The retention part moreover comprises a central post corresponding to the holder of the head. The cap, in turn, is also substantially cup-shaped, wherein the inner side of its rim is formed in accordance with the outer side of the rim of the retention part. For connecting the prosthesis structure with the implant structure, normally first the retention part is pressed into the cap, wherein the rim of the retention part is deformed inwardly and expands again when the retention part is arranged in the cap. Then, the cap together with the retention part is pressed onto the head of the implant structure, wherein both the rim and the post of the retention part are deformed and expand as much as possible when the prosthesis structure is arranged on the head of the implant structure.

A problem nowadays often occurring in artificial dentures is the fact that the position of the dental implant or the implant structure depends on various factors, for example the condition of the jaw bone, the progress of a possible osseointegration and in particular also an exact insertion. Accordingly, nowadays it is regularly not possible to place implant structures exactly at a desired target place and in a desired target position and connect them with the prosthesis structure. This problem is of additional relevance in prosthesis structures which, for example, are intended for replacing a plurality of teeth and which are connected with the jaw bone of the patient via a plurality of implant structures that are parallelized as much as possible.

In order to nevertheless allow a reliable connection of the prosthesis structure with the implant structure, the mentioned connection mechanisms are partly configured so as to allow to a certain extent a compensation for diverging implanted implant structures. For example, the retention parts of the described snap-engagement systems are typically relatively soft and elastic so that it is to a certain extent possible to compensate for axial divergences of implant structures implanted in a disparallel manner. Sometimes also sets of analogous retention parts made of materials having different hardnesses are marketed so that during fitting the prosthesis structure it is possible to select appropriate retention parts depending on the degree of disparallelism of the implant structures. For such a selection and adaptation of the retention parts during fitting of the prosthesis structure, however, it is often necessary to test different hardnesses of retention parts, which can be difficult and laborious. Moreover, when being mounted in and dismounted from the corresponding caps, the retention parts are also squeezed and damaged due to the mentioned deformation, which can lead to a high consumption of retention parts. Moreover, during everyday use of the prosthesis structure and as a consequence of the mentioned compensation function, the retention bodies are strained so much by deformation as well as a non-uniform mounting and dismounting of the prosthesis structure that they have to be renewed regularly, which can be laborious and expensive. Finally, dirt particles can collect in the hollow spaces formed by the deformation of the retention parts, which is mostly not desired.

Therefore, it is an object of the present invention to suggest a connection device for connecting a prosthesis structure with an implant structure or a capped tooth as well as a corresponding retention insert, by means of which a prosthesis structure can be mounted and dismounted relatively easily and efficiently in the mouth of a patient, which can be adapted relatively easily to the specific conditions, and in which retention inserts can be renewed relatively easily and gently.

DESCRIPTION OF THE INVENTION

According to the invention, this object is achieved by a connection device as defined in independent claim 1, a retention insert as defined in independent claim 13, a method as defined in independent claim 14. Advantageous embodiments of the invention are described hereinbelow.

The gist of the invention is the following: A connection device for connecting a prosthesis structure with an implant structure or a capped tooth comprises a holding shell and a retention insert. The retention insert comprises an end side and a substantially ring-shaped retention rim projecting therefrom and the holding shell comprises an end side and a substantially ring-shaped holding rim projecting therefrom. The holding rim and the end side of the holding shell form a retainer in which the retention insert can be arranged such that an outer surface of the retention rim of the retention insert is located adjacent to an inner surface of the holding rim of the holding shell. The outer surface of the retention rim of the retention insert is arranged at least partly in a manner spaced from and adjacent to the inner surface of the holding rim of the holding shell when the retention insert is arranged in the retainer of the holding shell and when essentially no radial forces are acting on the holding rim of the holding shell and on the retention rim of the retention insert. In this connection, the term "radial forces" refers to forces acting radially with respect to the holding rim and/or the retention rim such that the holding rim is pressed in the direction of the retention rim and/or in particular the retention rim is pressed in the direction of the holding rim. Depending on the initial situation, implant structures and capped teeth can be used alternatively with respect to each other. In the following, capped teeth are not mentioned explicitly. However, they are comprised as an alternative when implant structures are mentioned. In particular, in the following the term "implant structure" in this connection also comprises capped teeth.

The connection device can be provided in particular as a female part of a snap-engagement connection. Connection devices of this kind can have a total width between about 9 mm and about 3 mm or between about 7 mm and about 4 mm or between about 6 mm and about 5 mm and in particular of about 5.5 mm. Moreover, they can have a height between about 1 mm and about 3 mm or between about 1.5 mm and about 2.5 mm and in particular of about 2 mm. The outer surface of the retention rim and the inner surface of the holding rim can have any suitable shape, for example a substantially planar shape or substantially curved shape. The prosthesis structure can in particular be a prosthesis for a plurality of teeth. By using the connection device, the holding shell can be firmly connected with the prosthesis structure, for example it can be cast into a synthetic prosthesis material. For allowing an appropriate connection with the prosthesis structure, the holding shell can also comprise suitable means such as one or more notches on its outer surface. The implant structure can consist of one or more parts, wherein it can comprise, e.g., a screw-shaped implant body and a connector or abutment arranged thereon. The abutment can have a head with a male part of a snap-engagement connection. The holding shell and the retention insert can be substantially cup-shaped and in particular suitable for being connected with a male part of the implant structure. The end sides of the holding shell and the retention insert can be substantially disk-shaped and have an opening or be completely closed. The holding rim can project substantially at a right angle from the circumference of the end side of the holding shell.

In that the adjacent outer surface of the retention rim and inner surface of the holding rim are at least partly not contacting each other but are spaced from each other when essentially no radial forces are acting on the holding rim of the holding shell and on the retention rim of the retention insert, it can, i.a., be achieved that the retention insert is connected relatively loosely with the holding shell when the connection device has not yet been placed on the implant structure. Advantageously, this loose connection is just sufficient for holding the retention insert in the holding shell to thus allow a comfortable handling. This loose connection can allow the retention insert to be relatively easily removed from and inserted in the holding shell without having to be substantially deformed or strained in any other way. Thus, it is possible to insert and remove the retention insert gently, which can improve the flexibility and lifetime of the connection device.

When the connection device is then connected with the implant structure as intended, for example such that a male head is inserted or snapped in the retention body, radial forces can act from the head on the retention rim of the retention body. These forces can press the retention rim in the direction of the holding rim of the holding shell so that the retention rim is moved in the direction of the holding rim. Thereby, it can be moved in a resilient manner in the direction of the holding rim without being considerably squeezed or similarly deformed. Thus, the retention body can be firmly connected with the holding shell when the prosthesis structure is connected by means of the connection device with the implant structure. At the same time, a spring force can act from the moved retention rim on the head so that the connection device is clamped on the head. Moreover, the retention rim of the retention body can return resiliently into its original position after the prosthesis structure has been removed from the implant structure so that the retention body is relatively little strained and can have a relatively long lifetime. Finally, the retention rim can also be moved in a non-uniform manner along the circumference in the direction of the holding rim so that an inaccurate position of the implant structure and in particular disparallelism can be compensated for without the retention body being substantially squeezed or similarly deformed.

Preferably, in the connection device the outer surface of the retention rim of the retention insert is at least partly arranged so as to be spaced from and adjacent to the inner surface of the holding rim of the holding shell in that the outer surface of the retention rim of the retention insert is more strongly inclined in the direction of a central axis of the connection device than the inner surface of the holding rim of the holding shell. In this connection, the "central axis" corresponds to the central axis or longitudinal axis or rotational axis of the holding shell or retention insert which extends substantially perpendicular with respect to the respective end side, wherein it extends in particular perpendicularly through the center of the respective end side in case this end side is, e.g., substantially disk-shaped. In this connection, the term "inclined in the direction of the central axis of the connection device" relates to an inclination of the outer surface of the retention rim or the inner surface of the holding rim relative to the corresponding end side. This inclination can correlate with an angle between the outer surface of the retention rim or the inner surface of the holding rim and the corresponding end side, wherein in this case the angle between the outer surface of the retention rim and the corresponding end side is, in accordance with the invention, smaller than the angle between the inner surface of the holding rim and the corresponding end side. The mentioned stronger inclination of the outer surface of the retention rim as compared to the inclination of the inner surface of the holding rim can lead to a space being formed between the outer surface of the retention rim and the inner surface of the holding rim, wherein said space can increase in size starting from the corresponding end side. In accordance with the invention, the adjacent outer surface of the retention rim and inner surface of the holding rim thus at least partly do not contact each other but are spaced from each other when the retention insert is arranged in the retainer of the holding shell and when essentially no radial forces are acting on the holding rim of the holding shell and on the retention rim of the retention insert.

The retention rim of the retention insert of the connection device advantageously comprises recesses which start on an end of the retention rim facing away from the end side of the retention insert and extend in the direction of the end side of the retention insert. The retention rim can also have lamellae and recesses alternating in the circumferential direction. Such recesses can serve for determining the deformability or resiliency and thus the degree of hardness of the retention insert for a given material. In particular, analogous retention inserts can be provided with a different number of recesses, wherein the hardness of the retention inserts increases as the number of recesses decreases. The different degrees of hardness of retention inserts of the same kind can be indicated easily by differently colored retention inserts.

Preferably, the recesses in the retention rim of the retention insert of the connection device extend over at least about 50% of the width of the retention rim of the retention insert, preferably over at least about 70% of the width of the retention rim of the retention inert and in particular over at least about 80% of the width of the retention rim of the retention insert. Such recesses can allow an appropriate elastic movability of the lamellae arranged between the retainers. The retention rim of the retention insert preferably comprises three, four, five, six or more recesses. Such a number of recesses allows a regular arrangement in the circumferential direction and entails that the retention insert can be manufactured relatively easily.

Advantageously, the retention rim of the retention insert of the connection device comprises a projection projecting radially from the outer surface of the retention rim of the retention insert and the holding rim of the holding shell comprises a corresponding groove extending radially from the inner surface of the holding rim of the holding shell. The projection and the groove can extend in particular along substantially the entire circumference of the retention rim or the holding rim. By means of such a projection and such a corresponding groove it can be achieved relatively easily that the retention insert is firmly connected with the holding shell when the retention insert is arranged in the retainer of the holding shell and a radial force is acting on the holding rim of the holding shell and/or on the retention rim of the retention insert.

Thereby, the projection of the retention rim of the retention insert is preferably arrangeable in the groove of the holding rim of the holding shell in such a manner that the retention insert is releasably held in the holding shell when the retention insert is arranged in the retainer of the holding shell and when essentially no radial forces are acting on the holding rim of the holding shell and on the retention rim of the retention insert. In particular, the projection can thus be arranged only partly in the groove when essentially no radial forces are acting on the holding rim of the holding shell and on the retention rim of the retention insert so that the retention insert is held firmly enough in the holding shell for being held therein but is nevertheless held loosely enough in the holding shell for being easily removable from the holding shell.

Preferably, the projection of the retention rim of the retention insert comprises a substantially planar projection supporting surface and the groove of the holding rim of the holding shell comprises a substantially planar groove supporting surface, wherein a part of the projection supporting surface contacts a part of the groove supporting surface when the retention insert is arranged in the retainer of the holding shell and when essentially no radial forces are acting on the holding rim of the holding shell and on the retention rim of the retention insert, and wherein the groove supporting surface is rounded towards its end facing the retention insert and/or the projection supporting surface is rounded towards its end facing the holding shell. In particular, the groove supporting surface can be rounded away from the projection supporting surface and the projection supporting surface can be rounded away from the groove supporting surface. The projection supporting surface of the projection of the retention insert can in particular be configured so as to face substantially away from the end side of the retention insert and the groove supporting surface of the groove of the holding shell can be configured so as to face substantially towards the end side of the holding shell. s By means of such a rounded groove supporting surface and/or projection supporting surface, an appropriate supporting but nevertheless easily releasable connection between retention insert and holding shell can be realized.

Advantageously, the projection of the retention rim of the retention insert can be arranged in the groove of the holding rim of the holding shell such that the retention insert is permanently connected with the holding shell when the retention insert is arranged in the retainer of the holding shell and when a radial force is acting on the retention rim of the retention insert in the direction of the holding rim of the holding shell and/or on the holding rim of the holding shell in the direction of the retention rim of the retention insert. For example, when a force is acting on the holding rim in the direction of the retention rim and/or in particular a force is acting on the retention rim in the direction of the holding rim, the holding rim and the retention rim can be moved relative to each other such that the projection is further or completely arranged in the groove and the retention insert is thus permanently or firmly connected with the holding shell. The radial force can be applied to the retention rim or maintained by a male part of the head of the implant structure.

The retention rim of the retention insert of the connection device preferably comprises an inner surface opposite to the outer surface, wherein the inner surface is rounded towards the end facing away from the end side of the retention insert. By means of such a rounded shape of the retention rim it is possible that, on the one hand, the connection device is centered when being placed on the male part of the snap-engagement connection or the head of the implant structure and, on the other hand, during this placement a force is continuously applied to the retention rim in the direction of the holding rim. This force is maintained even after the placement is completed so that the retention rim is pressed and moved in the direction of the holding rim and thus a permanent or firm connection between retention insert and holding shell is possible.

Preferably, the retention insert and/or the holding shell is/are made of a biocompatible polymeric material, in particular a polyetheretherketone. Thereby, the polyetheretherketone can be a polyetheretherketone admitted by an official authority for an at least thirty days stay in mouth. Such a polyetheretherketone can additionally be colored appropriately. Other possible biocompatible materials are polyamides such as polyhexamethylene adipic acid amide. Connection devices of this kind can be manufactured easily. Moreover, it is possible to manufacture in particular also the holding shells of a light-colored, preferably gingiva-colored material so that the connection device is preferably not readily visible in the mouth of a patient. Moreover, such connection devices can also be used in holistic medicine in which there are specific requirements as to the materials to be used and in particular the use of titanium is not admitted. Alternatively, however, the holding shell can also be made of titanium.

Preferably, an engagement groove is formed on said outer surface of said retention rim of said retention insert, which preferably extends over the entire circumference of said retention rim of said retention insert. Such an engagement groove allows the retention insert to be efficiently held by a suitable tool such as a mounting tool. For example, this can allow for a simple efficient demounting of the retention insert from the holding shell.

A further aspect of the invention relates to a retention insert of a connection device for connecting a prosthesis structure with an implant structure as described above.

Preferably, the retention insert comprises an end side and a substantially ring-shaped retention rim projecting therefrom and is adapted to be arranged in a retainer in the holding shell formed by a holding rim and an end side of the holding shell such that an outer surface of the retention rim of the retention insert is adjacent to an inner surface of the holding rim of the holding shell. The retention insert is configured such that the outer surface of the retention rim of the retention insert is at least partly spaced from and adjacent to the inner surface of the holding rim of the holding shell when the retention insert is arranged in the retainer of the holding shell and when essentially no radial forces are acting on the holding rim of the holding shell and on the retention rim of the retention insert. Advantageously, the retention insert is configured such that the outer surface of the retention rim of the retention insert is at least partly spaced from and adjacent to the inner surface of the holding rim of the holding shell in that the outer surface of the retention rim of the retention insert is more strongly inclined in the direction of a central axis of the connection device than the inner surface of the holding rim of the holding shell.

The retention rim preferably comprises recesses starting on an end facing away from the end side and extending in the direction of the end side. The recesses in the retention rim thus advantageously extend over at least about 50% of the width of the retention rim, preferably over at least about 70% of the width of the retention rim and in particular over at least about 80% of the width of the retention rim. The retention rim preferably comprises three, four or six recesses.

The retention rim advantageously comprises a projection projecting radially from the outer surface of the retention rim, wherein the projection is configured so as to correspond to a groove extending from the inner surface of the holding rim of the holding shell. The projection of the retention rim can preferably be arranged such in the groove of the holding rim of the holding shell that the retention insert is releasably held in the holding shell when the retention insert is arranged in the retainer of the holding shell and when essentially no radial forces are acting on the holding rim of the holding shell and on the retention rim of the retention insert. The projection of the retention rim of the retention insert preferably comprises a substantially planar projection supporting surface, wherein a part of the projection supporting surface contacts a part of a substantially planar groove supporting surface of the groove of the holding rim of the holding shell when the retention insert is arranged in the retainer of the holding shell and when essentially no radial forces are acting on the holding rim of the holding shell and on the retention rim of the retention insert, and wherein the projection supporting surface is rounded towards its end facing the holding shell. The projection of the retention rim is advantageously configured such that it can be arranged in the groove of the holding rim of the holding shell in such a manner that the retention insert is permanently connected with the holding shell when the retention insert is arranged in the retainer of the holding shell and when a radial force is acting on the retention rim of the retention insert in the direction of the holding rim of the holding shell and/or on the holding rim of the holding shell in the direction of the retention rim of the retention insert.

The retention rim preferably comprises an inner surface opposite to the outer surface, wherein the inner surface is rounded towards the end facing away from the end side of the retention insert. Preferably, the retention insert is made of a biocompatible polymeric material, in particular of a polyetheretherketone. Preferably, an engagement groove is formed on said outer surface of said retention rim of said retention insert, which preferably extends over the entire circumference of said retention rim of said retention insert.

Another further aspect of the invention relates to a method for connecting a prosthesis structure with an implant structure by means of a connection device as described above, wherein the holding shell of the connection device is firmly mounted to the prosthesis structure and wherein the implant structure comprises a head being configured for a snap-engagement connection. As discussed above with respect to the connection device, the term "implant structure" in this respect also comprises capped teeth. The method comprises the steps of inserting the retention insert of the connection device axially into the holding shell of the connection device until the retention insert is arranged in the holding shell; arranging the prosthesis structure at the implant structure so that the head of the implant structure contacts the retention insert of the connection device; and pressing the prosthesis structure on the implant structure so that the retention insert is pressed axially on the head of the implant structure, wherein a radial force is acting on the retention rim of the retention insert so that the retention rim is moved at least partly in the direction of the holding rim of the holding shell. By means of such a method, the prosthesis structure can be relatively easily, comfortably and reliably placed or snapped on the implant structure in a releasable manner. At the same time, the retention inserts are relatively little strained and can be replaced relatively easily.

A further other aspect of the invention relates to a mounting tool for demounting a retention insert from a holding shell of a connection device as described above. The mounting tool comprises a sleeve-shaped demounting head which is arrangeable between an outer surface of a retention rim of the retention insert and an inner surface of a holding rim of the holding shell when the retention insert is arranged in a retainer of the holding shell. Such a mounting tool allows for a simple and efficient demounting of the retention insert from the holding shell without impairing the retention insert. Preferably, an inner side of the demounting head is conical so that the retention rim of the retention insert is moved in the direction of a central axis of the connection device when the demounting head of the mounting tool is arranged between the outer surface of the retention rim of the retention insert and the inner surface of the holding rim of the holding shell. By means of such a mounting tool, the retention rim can be moved inwardly or in the direction of the central axis in such a resilient manner that the retention insert is no longer held in the holding shell and thus can be removed from the retention shell without difficulty. In particular, a projection of the retention insert can be moved essentially completely out of a groove of the holding shell so that the retention insert is no longer connected with the holding shell.

Preferably, a distal end of the demounting head of the mounting tool has a tapered shape. Such a tapered shape of the demounting head allows the demounting head to be centered and inserted easily between the retention rim and the holding rim. Said demounting head preferably comprises an engagement portion for engaging a corresponding engagement groove of said retention insert. Such an engagement portion allows for providing a holding force between the retention insert and the mounting tool such that the retention insert can conveniently be removed from the holding shell.

Preferably, the mounting tool comprises a mounting head which has an insertion portion being arrangeable in a retainer formed by said retention rim of said retention insert and an end side of said retention insert, such that said retention insert is held at said mounting head. Such a mounting tool allows for a particularly suitable mounting and at the mean time a particularly suitable demounting. In particular, the insertion portion can be shaped in correspondence with the retainer of the retention insert such that the retention insert can be held in an essentially form-fit manner by the mounting tool. Therefore, a radial outer surface of said insertion portion of said mounting head preferably is convexly curved. Preferably, the mounting tool has an elongated basic form wherein said mounting head is arranged at one of its longitudinal ends and said demounting head at the other of its longitudinal ends. Such an arrangement of the mounting tool allows for providing the mounting tool in an appropriate compact shape.

BRIEF DESCRIPTION OF THE DRAWINGS

In the following, the connection device according to the invention, the retention insert according to the invention, the mounting tool according to the invention and the method according to the invention are described in more detail with reference to the attached drawings and on the basis of embodiments, wherein.

WAY(S) FOR CARRYING OUT THE INVENTION

Figure 1:
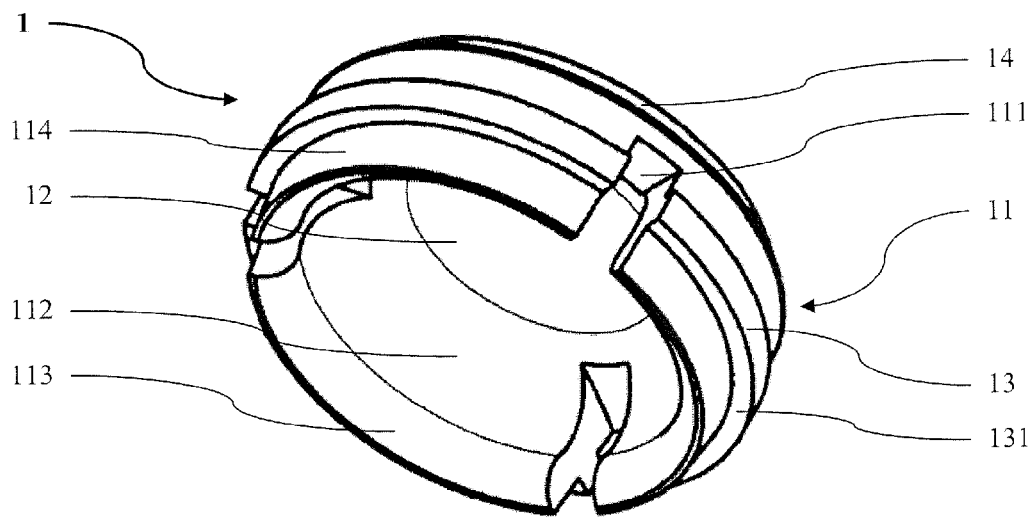
FIG. 1 shows a perspective view of a first embodiment of a retention insert according to the invention of a first embodiment of a connection device according to the invention.

In the following description, specific expressions are used for practical reasons and are not to be understood as being restrictive. The terms "right", "left", "bottom" and "top" refer to directions in the drawing to which reference is made. The terms "inwardly" and "outwardly" refer to directions towards or away from the geometrical center of the connection device and named parts thereof. The terminology comprises the terms explicitly mentioned above, derivations thereof and terms having a similar meaning.

FIG. 1 shows a first embodiment of a retention insert 1 according to the invention. The substantially cup-shaped retention insert 1 comprises a substantially disk-shaped closed end side 12 and a substantially ring-shaped retention rim 11 projecting at the circumference thereof at an angle. The retention rim 11 comprises an outer surface 114, three recesses 111 uniformly spaced from each other in the circumferential direction, and lamella portions 112 arranged therebetween. The recesses 111 start from an end of the retention rim 11 facing away from the end side 12 and extend in the direction of the end side 12 over more than 80% of the retention rim 11. The lamella portions 112 comprise an inner surface describing an inner surface of the retention rim 11 opposite to the outer surface 114. The inner surfaces of the lamella portions 112 are rounded outwardly towards the open end of the retention inert 1, i.e. towards the end of the retention insert 1 facing away from the end side 12, and thus comprise a correspondingly curved portion 113.

A step 14 extending along the entire circumference is formed at the peripheral upper rim of the end side 12. Approximately in the center of the retention rim 11 there is provided a bar-shaped projection 13 projecting radially from the outer surface 114 of the retention rim 11 and extending along the entire circumference of the lamella portions 112 of the retention dm 11. The projection 13 comprises a planar radial outer side, a planar upper side being at a right angle thereto and facing the end side 12, and a planar bottom side being at a right angle thereto, facing away from the end side 12 and describing a projection supporting surface 131. The retention insert 1 is completely made of polyetheretherketone, wherein alternatively also a different biocompatible polymeric or non-polymeric material can be used.

For the entire further description, the following is true: If a Figure comprises reference signs for the sake of clarity of the drawing and if these reference signs are not mentioned in the directly corresponding text of the description, reference is made to the explanation thereof in previous descriptions of the Figures. Moreover, if reference signs are mentioned in the text of the description directly relating to a Figure and if these reference signs are not contained in the corresponding Figure, reference is made to the previous Figures.

Figure 2:
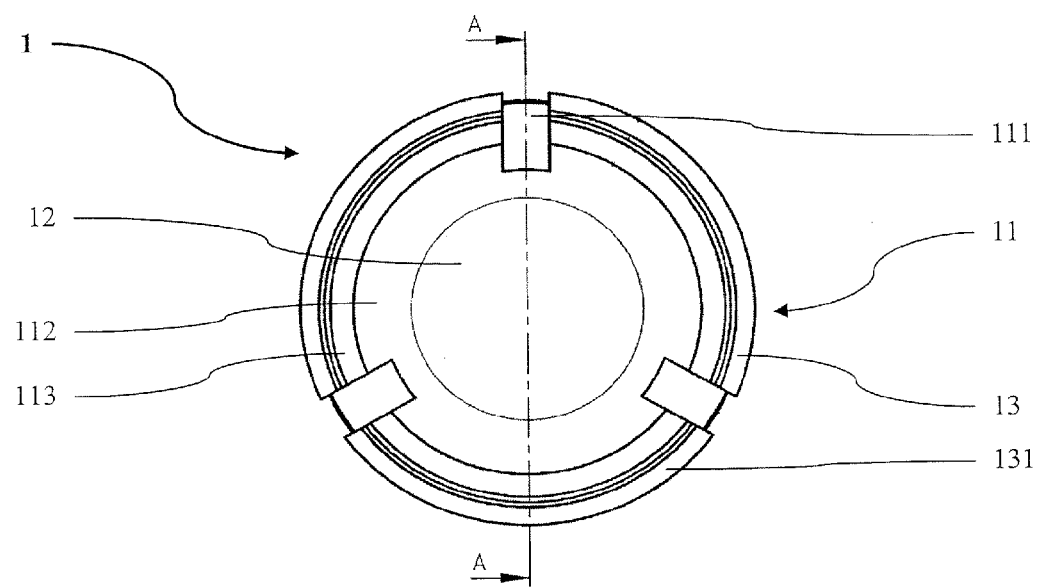
FIG. 2 shows a bottom view of the retention insert of FIG. 1.

FIG. 2 shows the retention insert 1 from a bottom or from an open side. It is evident therein that the projection 13 projects from the rest of the retention inset 1 radially outwardly so that in the view of FIG. 2 the projection supporting surface 131 of the projection is completely visible. It is also evident that the three recesses 111 are uniformly distributed across the circumference at an angle of about 120° relative to one another. Furthermore, in combination with FIG. 1 it is evident that the lamella portions 112 of the retention rim 11 start from the substantially disk-shaped end side 12. Its inner surfaces each have an upper portion which is curved inwardly with a positive radius of curvature and which transitions into the portion 113 which is curved outwardly with a negative radius of curvature.

Figure 3:
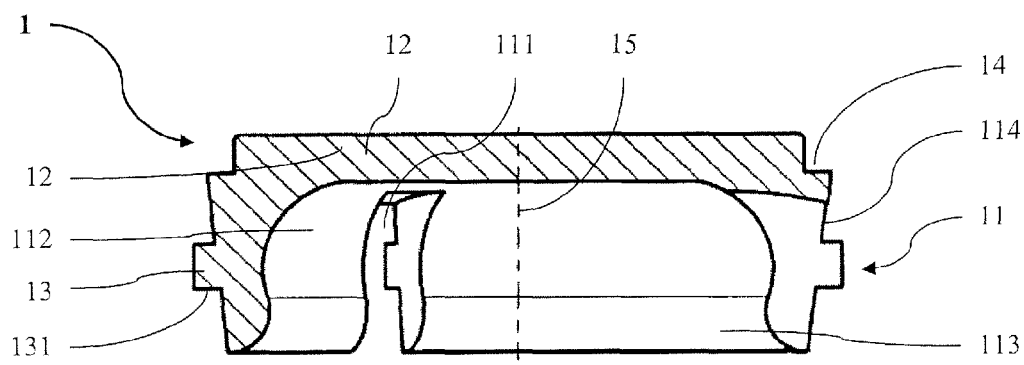
FIG. 3 shows a cross-sectional view along the line A-A of the retention insert of FIG. 2.

FIG. 3 shows a cross-sectional view of the retention insert 1. The step 14 comprises two surfaces being arranged at a right angle relative to one another, wherein one of these surfaces is directed outwardly and the other one towards the top. The outer surface 114 of the retention rim 11 is angled relative to the end side 12 such that it is inclined inwardly in the direction of a central axis 15 of the retention insert 1. The outer surface 114 and the end side 12 enclose an acute angle between 82° and 85°, or between 83° and 84°, preferably of about 83.3°.

Figure 4:
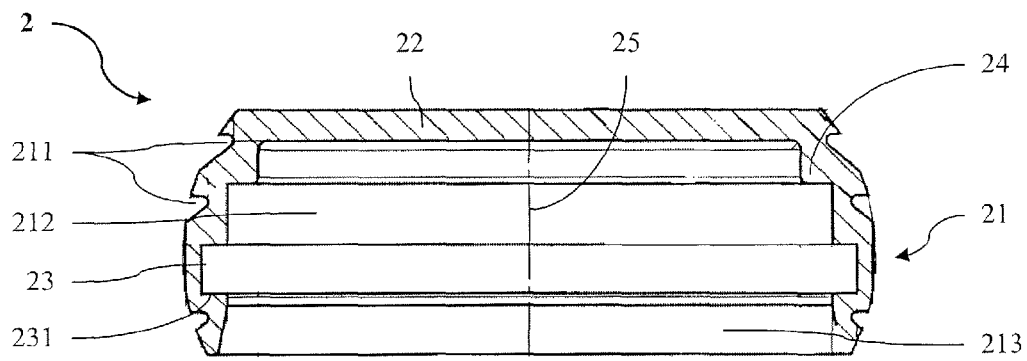
FIG. 4 shows a cross-sectional view of a first embodiment of a holding shell of the first embodiment of a connection device.

FIG. 4 shows an embodiment of a substantially cup-shaped holding shell 2 comprising a substantially disk-shaped closed end side 22 and a substantially ring-shaped holding rim 21 projecting therefrom in an angled manner at the circumference. The holding rim 21 comprises an inner surface 212 and three notches 211 formed at an outer side that is bulged outwardly, said notches being arranged at different heights and extending along the entire circumference of the holding rim 21. The inner surface 212 of the holding rim 21 is at a right angle with respect to the end side 22, wherein it transitions towards the bottom open end of the holding shell 2 into an outwardly inclined portion 213. At the transition between end side 22 and holding rim 21 there is provided a step 24 having a planar inner side facing a central axis 25 and a planar bottom side being at a right angle thereto and facing the bottom open end of the holding shell 2. From the inner surface 212 of the holding rim 21, a groove 23 is formed in the holding rim 21, said groove comprising an inner surface, a bottom surface being at a right angle thereto and facing away from the end side 22, and a groove supporting surface 231 also being at a right angle thereto and facing the end side 22. The holding shell 2 is completely made of polyetheretherketone, wherein alternatively also a different biocompatible polymeric or non-polymeric material can be used, for example titanium.

Figure 5:
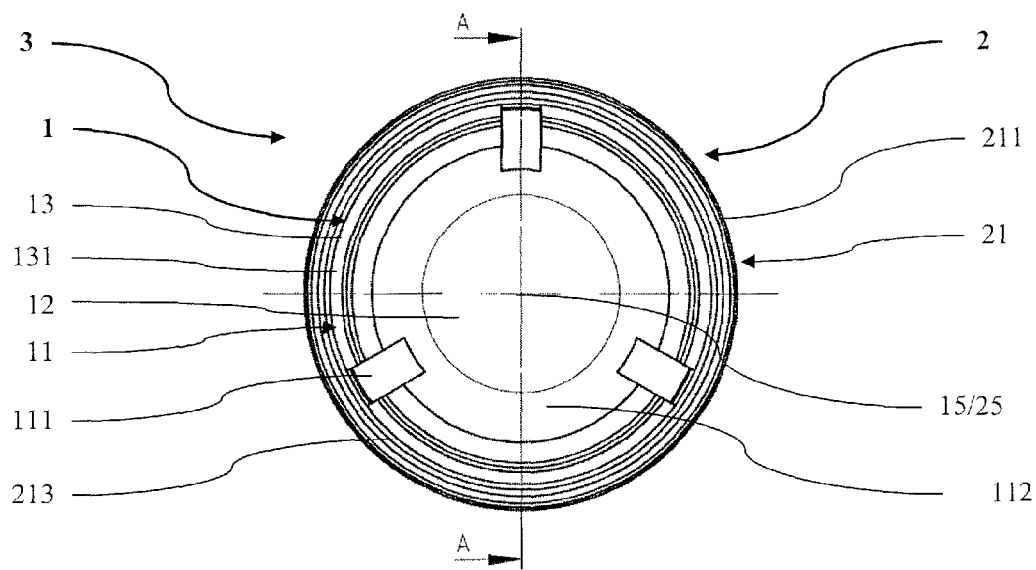
FIG. 5 shows a bottom view of the first embodiment of a connection device, wherein the retention insert of FIG. 1 is arranged as intended in the holding shell of FIG. 4.
Figure 6:
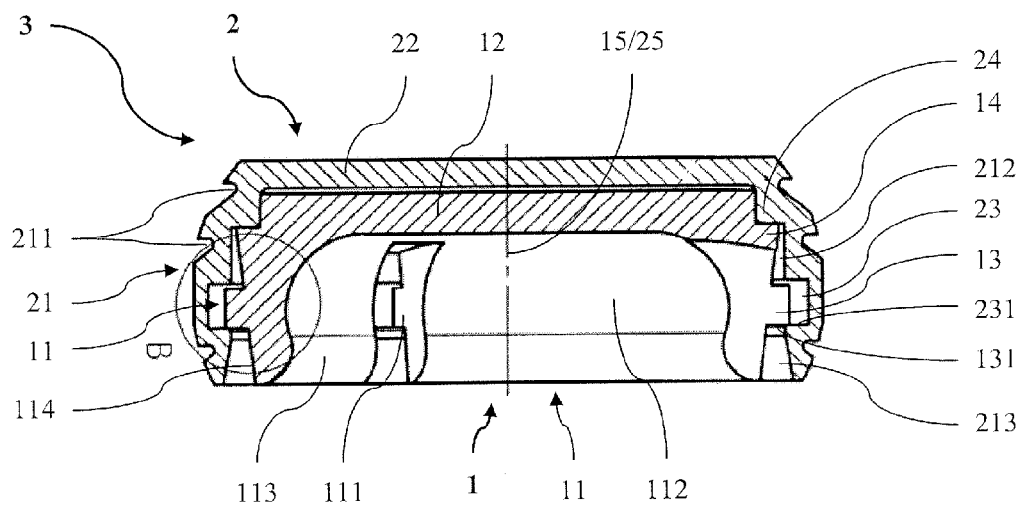
FIG. 6 shows a cross-sectional view along the line A-A of the connection device of FIG. 5.

FIG. 5 and FIG. 6 show a first embodiment of a connection device 3 according to the invention, which comprises the retention insert 1 and the holding shell 2. The retention insert 1 is inserted, starting with its end side 12, through the open side of the holding shell 2 so far into the holding shell 2 until the step 14 of the retention insert 1 contacts the step 24 of the holding shell 2. During this insertion, the inclined portion 213 of the inner surface 212 of the holding rim 21 serves for centering and guiding the retention insert 1 relative to the holding shell 2. The central axis 15 of the retention insert 1 and the central axis 25 of the holding shell 2 lie at the same place and together form a central axis of the connection device 3.

By forming the inner surface 212 of the holding rim 21 of the holding shell 2 in a manner inclined at a right angle relative to the end side 22 of the holding shell 2 and the outer surface 112 of the retention rim 11 of the retention insert 1 in a manner inclined at an acute angle in the direction of the central axis 15, 25, a space which increases towards the bottom or in the direction of the open side of the connection device 1 is formed between the inner surface 212 of the holding rim 21 and the outer surface 112 of the retention rim 11. This space allows the projection 13 of the retention insert 1 to lie only partly in the groove 23 of the holding shell 2. Thus, the retention insert 1 is held releasably in the holding shell 2 and the connection device 1 forms a unit.

Figure 7:
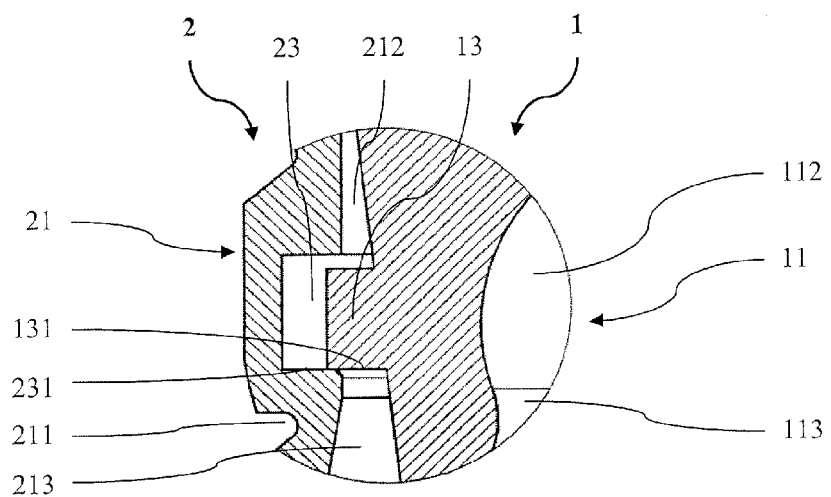
FIG. 7 shows a cross-sectional view of the detail B of the connection device of FIG. 6.

FIG. 7 shows a detail of the connection device 3, in which in particular the arrangement of the groove 23 in the holding shell 2 and the projection 13 of the retention insert are shown in detail in a state in which essentially no radial forces are acting on the holding rim 21 of the holding shell 2 and on the retention rim 11 of the retention insert 1 (for example a first position). The groove supporting surface 231 of the groove 23 is curved downwardly in the direction of the central axis 15, 25. This curvature allows the projection 13 to be removable from the groove 23 smoothly and with relatively little force required. Thus, the retention insert 1 can be removed comfortably and easily from the holding shell 2. FIG. 7 moreover shows that the groove 23 is higher than the projection 13. Due to this shape, an outwardly swiveling movement of the retention rim 11 is not impaired by the groove 23 because during such a swiveling movement the projection 13 is not only moved outwardly but also slightly upwardly.

By applying the connection device 3, the holding shell 2 is mounted firmly to a prosthesis structure. To this end, it can, e.g, be cast in a synthetic prosthesis material, wherein the notches 211 of the holding rim 21 contribute to a reliable firm connection between holding shell 2 and prosthesis structure. Furthermore, an implant structure having a head that is designed for a snap-engagement connection is engrafted in a jaw bone as intended. Before connecting the prosthesis structure with the implant structure, the retention insert 1 is moved axially into the holding shell 2 until the retention insert 1 is arranged or held in the holding shell 2. The retention insert 1 is clamped by the step 14 and the projection supporting surface 131 between the step 24 of the holding shell and the groove supporting surface 231 so that the retention insert 1 is held in the holding shell 2 and thus the prosthesis structure (for example a second position).

The prosthesis structure is then arranged at the implant structure so that the head of the implant structure contacts the retention insert 1 of the connection device 3. Then, the prosthesis structure is pressed on the implant structure so that the retention insert 1 is pressed axially on the head of the implant structure. The connection device 3 is centered by the outwardly curved portion 113 of the retention rim 11. Moreover, a radial force increasing along this outwardly curved portion 113 is acting on the retention rim 11 so that the latter is moved in the direction of the holding rim 21. In particular, the acute angle between the outer surface 114 of the retention rim 11 and the end side 12 of the retention insert 1 is obtunded by bending the lamella portions 112 of the retention rim 11 resiliently outwardly. By means of the outwardly moved retention rim 11, the projection 13 is arranged such in the groove 23 that the retention insert 1 is permanently connected with the holding shell 2.

When the prosthesis structure is placed on the implant structure, the head of the implant structure is snapped in the connection device 3. The head is enclosed in the portion of the inner surface 112 of the retention rim 11 of the retention insert 1 which portion is curved inwardly with a positive radius of curvature, wherein it is held by the elastic or resilient forces of the retention rim 11 acting in the direction of the central axis and induced by the movement of the retention rim 11. Accordingly, the head is held the stronger the greater these elastic forces are. And these elastic forces depend, i.a., on the material of which the retention insert 1 is made and on the number and size of the recesses 111 of the retention rim 11.

Figure 8:
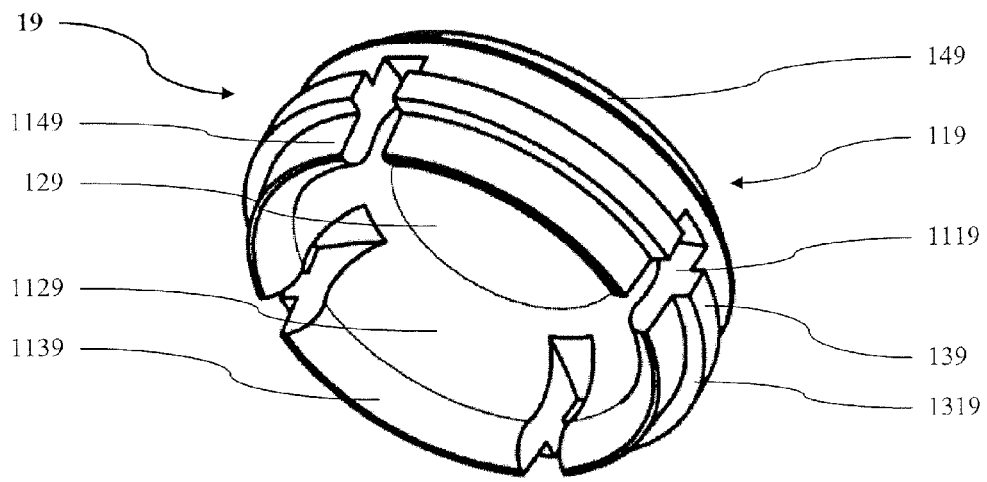
FIG. 8 shows a perspective view of a second embodiment of a retention insert according to the invention of a second embodiment of a connection device according to the invention.

FIG. 8 shows a second embodiment of a retention insert 19 according to the invention, which retention insert is designed substantially analogously to the retention insert 1 described above, except for the fact that it comprises a retention rim 119 having four recesses 1119. In particular, the retention insert 19 comprises an end side 129 as well as the retention rim 119 with an outer surface 1149, the four recesses 1119 spaced uniformly with respect to each other in the circumferential direction, as well as lamella portions 1129 arranged therebetween. The recesses 1119 are angled about 90° relative to each other. They start from an end of the retention rim 119 facing away from the end side 129 and extend in the direction of the end side 129 over more than 80% of the retention rim 119. The inner surfaces of the lamella portions 1129 have a curved portion 1139. The retention insert 19 further comprises a step 149 and a projection 139 having a projection supporting surface 1319. The retention insert 19 is completely made of polyether ether ketone. As the retention insert 19 has one recess 1119 more than the retention insert 1 described above, it is accordingly softer. For indicating this different hardness, the retention insert 19 can have a color different from that of retention insert 1.

Figure 9:
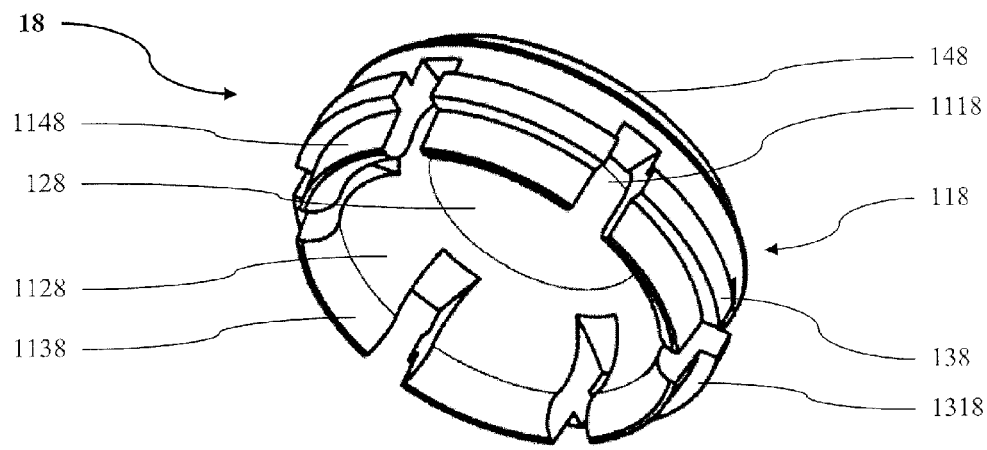
FIG. 9 shows a perspective view of a third embodiment of a retention insert according to the invention of a third embodiment of a connection device according to the invention.

FIG. 9 shows a third embodiment of a retention insert 18 according to the invention, which retention insert is designed substantially analogously to the retention inserts 1 and 19 described above, except for the fact that it comprises a retention rim 118 having six recesses 1118. In particular, the retention insert 18 comprises an end side 128 as well as the retention rim 118 with an outer surface 1148, the six recesses 1118 spaced uniformly with respect to each other in the circumferential direction, as well as lamella portions 1128 arranged therebetween. The recesses 1118 are angled about 60° relative to each other. They start from an end of the retention rim 118 facing away from the end side 128 and extend in the direction of the end side 128 over more than 80% of the retention rim 118. The inner surfaces of the lamella portions 1128 have a curved portion 1138. The retention insert 18 further comprises a step 148 and a projection 138 having a projection supporting surface 1318. The retention insert 18 is completely made of polyether ether ketone. As the retention insert 18 has more recesses 1118 than the retention inserts 1 and 19 described above, it is accordingly softer. For indicating this different hardness, the retention insert 18 can have a color different from that of retention inserts 1 and 19 described above.

Figure 10:
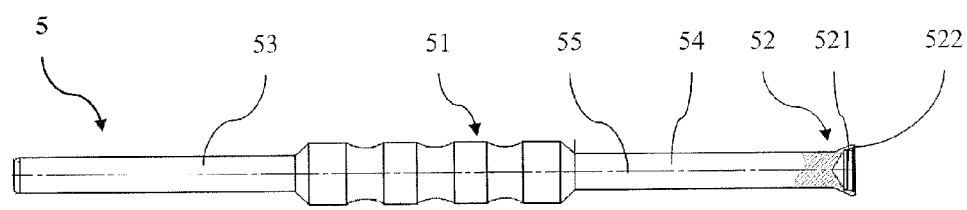
FIG. 10 shows a partial sectional side view of a first embodiment of a mounting tool according to the invention.

FIG. 10 shows a first embodiment of a mounting tool 5 according to the invention, which is substantially rotationally symmetric about a longitudinal axis 55. The mounting tool 5 comprises a shank-shaped cylindrical first portion 53 and a shank-shaped cylindrical second portion 54, which are connected with each other by a grip 51. At an end facing away from the grip 51, the second portion 54 transitions into a sleeve-shaped head 52. The head 52 comprises a hollow space formed by an inner side 521. The inner side 521 is conical so that the hollow space diminishes in the direction of the second portion 54. The distal end 522 of the head 52, which faces away from the second portion 54, is tapering.

For removing a retention insert from a holding shell of a connection device according to the invention, the distal end 522 of the head 52 can be inserted between a retention rim of the retention insert and a holding rim of the holding shell. Due to the conical shape of the inner side 521 of the head 52, the retention rim is moved more and more inwardly so that the retention insert is held less and less in the holding shell. When the head 52 is inserted in the connection device in the manner appropriate for demounting, the retention insert can thus be removed relatively easily from the holding shell.

Figure 11:
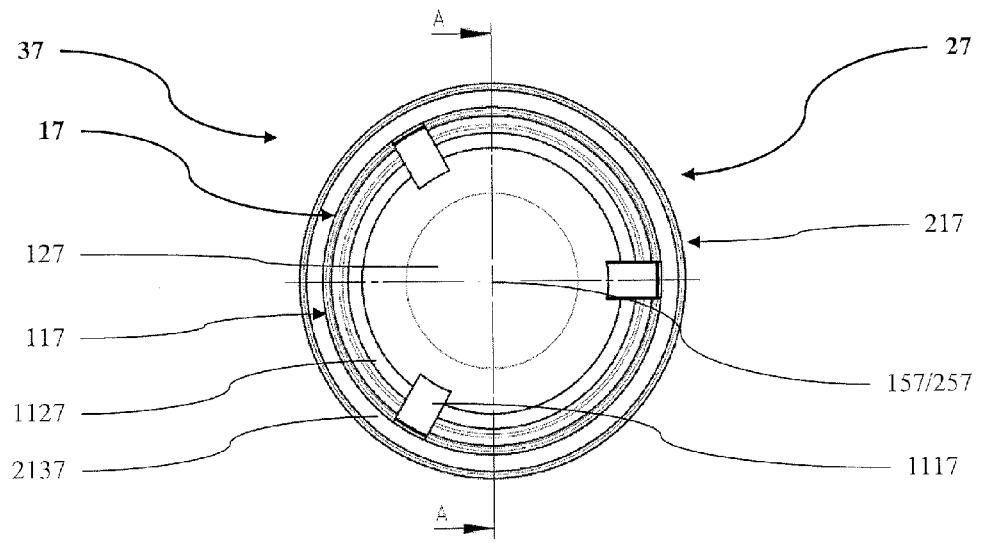
FIG. 11 shows a bottom view of a second embodiment of a connection device according to the invention with a second embodiment of a holding shell and a fourth embodiment of a retention insert according to the invention.
Figure 12:
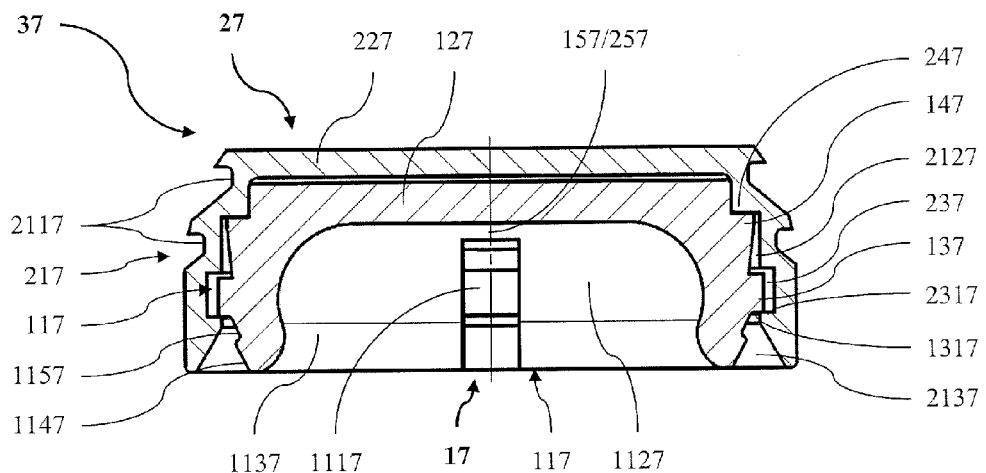
FIG. 12 shows a cross-sectional view along the line A-A of the connection device of FIG. 11.

FIG. 11 and FIG. 12 show a second embodiment of a connection device 37 according to the invention with a second embodiment of a holding shell 27 and a fourth embodiment of a retention insert 17 according to the invention. The substantially cup-shaped retention insert 17 comprises a substantially disk-shaped closed end side 127 and a substantially ring-shaped retention rim 117 projecting at the circumference thereof at an angle. The retention rim 117 comprises an outer surface 1147, three recesses 1117 uniformly spaced from each other in the circumferential direction, and lamella portions 1127 arranged therebetween. The recesses 1117 start from an end of the retention rim 117 facing away from the end side 127 and extend in the direction of the end side 127 over more than 80% of the retention rim 117. The lamella portions 1127 comprise an inner surface describing an inner surface of the retention rim 117 opposite to the outer surface 1147. The inner surfaces of the lamella portions 1127 are rounded outwardly towards the open end of the retention insert 17, i.e. towards the end of the retention insert 17 facing away from the end side 127, and thus comprise a correspondingly curved portion 1137.

A step 147 is formed at the peripheral upper rim of the end side 127 extending along the entire circumference. Approximately in the center of the retention rim 117 there is provided a bar-shaped projection 137 projecting radially from the outer surface 1147 of the retention rim 117 and extending along the entire circumference of the lamella portions 1127 of the retention rim 117, The projection 137 comprises a planar radial outer side, a planar upper side being at a right angle thereto and facing the end side 127, and a planar bottom side being at a right angle thereto, facing away from the end side 127 and describing a projection supporting surface 1317. Below the projection 137 an engagement groove 1157 is arranged on the outer surface 1147 of the retention rim 117. The retention insert 17 is completely made of polyetheretherketone, wherein alternatively also a different biocompatible polymeric or non-polymeric material can be used.

The substantially cup-shaped holding shell 27 comprises a substantially disk-shaped closed end side 227 and a substantially ring-shaped holding rim 217 projecting therefrom in an angled manner at the circumference. The holding rim 217 comprises an inner surface 2127 and two notches 2117 formed at an outer side being arranged at different heights and extending along the entire circumference of the holding rim 217. The inner surface 2127 of the holding rim 217 is at a right angle with respect to the end side 227, wherein it transitions towards the bottom open end of the holding shell 27 into an outwardly inclined portion 2137. At the transition between end side 227 and holding rim 217 there is provided a step 247 having a planar inner side facing a central axis 257 and a planar bottom side being at a right angle thereto and facing the bottom open end of the holding shell 27. From the inner surface 2127 of the holding rim 217, a groove 237 is formed in the holding rim 217, said groove comprising an inner surface, a bottom surface being at a right angle thereto and facing away from the end side 227, and a groove supporting surface 2317 also being at a right angle thereto and facing the end side 227. The holding shell 27 is completely made of polyetheretherketone, wherein alternatively also a different biocompatible polymeric or non-polymeric material can be used, for example titanium.

The retention insert 17 is inserted, starting with its end side 127, through the open side of the holding shell 27 so far into the holding shell 27 until the step 147 of the retention insert 17 contacts the step 247 of the holding shell 27. During this insertion, the inclined portion 2137 of the inner surface 2127 of the holding rim 217 serves for centering and guiding the retention insert 17 relative to the holding shell 27. Additionally, it allows for inserting suitable means between the holding rim 217 and the retention rim 117. A central axis 157 of the retention insert 17 and the central axis 257 of the holding shell 27 lie at the same place and together form a central axis of the connection device 37. By forming the inner surface 2127 of the holding rim 217 of the holding shell 27 in a manner inclined at a right angle relative to the end side 227 of the holding shell 27 and the outer surface 1127 of the retention rim 117 of the retention insert 17 in a manner inclined at an acute angle in the direction of the central axis 157, 257, a space which increases towards the bottom or in the direction of the open side of the connection device 17 is formed between the inner surface 2127 of the holding rim 217 and the outer surface 1127 of the retention rim 117. This space allows the projection 137 of the retention insert 17 to lie only partly in the groove 237 of the holding shell 27. Thus, the retention insert 17 is held releasably in the holding shell 27 and the connection device 17 forms a unit. Additionally, below the projection 137 the outer surface 1127 of the retention rim 117 of the retention insert 17 is arranged at a more acute angle than above the projection 137 which allows for a further improved convenient insertion of suitable means between the holding rim 217 and the retention rim 117.

Figure 13:
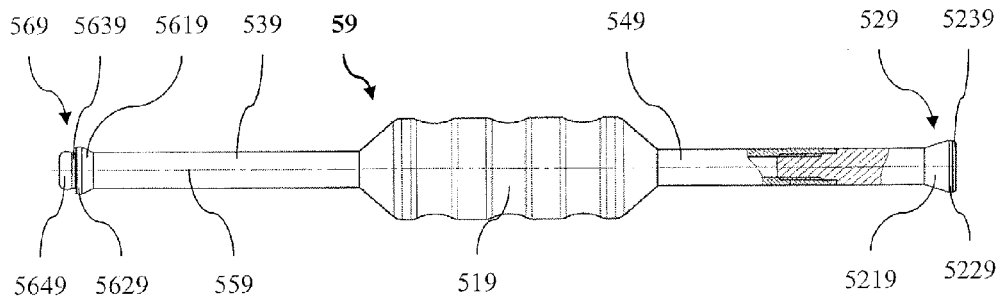
FIG. 13 shows a partial sectional side view of a second embodiment of a mounting tool according to the invention.

FIG. 13 shows a second embodiment of a mounting tool 59 according to the invention for mounting and demounting the retention insert 17 shown in FIG. 11 and in FIG. 12. The mounting tool 59 which in accordance with the mounting tool 5 shown in FIG. 10 is substantially rotationally symmetric about a longitudinal axis 559 comprises a shank-shaped cylindrical first portion 539 which at its one longitudinal end transitions into a mounting head 569 and at its other longitudinal end transitions into a grip 519. The mounting head 569 has a proximal conical portion 5619 transitioning into a cylindrical intermediate portion 5629. Adjacent to the intermediate portion 5629, the mounting head 569 comprises a cylindrical further portion 5639 having a smaller diameter than the intermediate portion 5629 such that the intermediate portion 5629 and the further portion 5639 together form a limit stop. Towards the distal end of the mounting head 569, the further portion 5639 transitions into an essentially cylindrical insertion portion 5649 having a convexly curved radial outer surface.

The mounting tool 59 further comprises a shank-shaped cylindrical second portion 549 which at its one longitudinal end transitions into a demounting head 529 and at its other longitudinal end transitions into the grip 519. The demounting head 529 has a hollow interior being opened into a distal direction. The hollow interior of the demounting head 529 is formed by an outwardly conically widening first portion 5219, a cylindrical second intermediate portion 5229 as well as an outwardly and into the direction of the opening narrowing engagement portion 5239.

Figure 14:
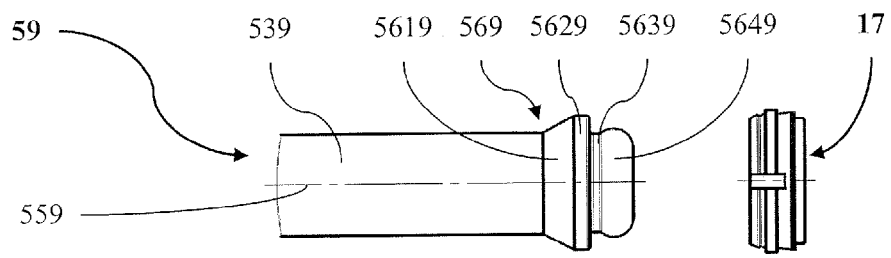
FIG. 14 shows a side view of a section of the mounting tool of FIG. 13 during mounting of the retention insert of the connection device of FIG. 11 before accommodating it.
Figure 15:
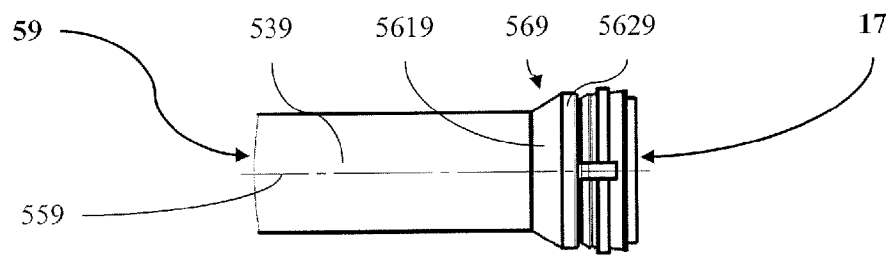
FIG. 15 shows a side view of the section of the mounting tool of FIG. 13 during mounting of the retention insert of the connection device of FIG. 11 after accommodating it.

As shown in FIG. 14, the mounting tool 59 is arranged with its mounting head 569 facing the open side of the retention insert 17 and axially spaced therefrom for mounting the retention insert 17. Afterwards, as shown in FIG. 15, the insertion portion 5649 as well as at least for the most part also the further portion 5639 of the mounting head 569 are pressed into the retainer of the retention insert 17. Thereby, the recesses 1117 of the retention rim 117 of the retention insert 17 allow for an elastic accommodation of the insertion portion 5649 of the mounting head 569. By means of the convex curving of the radial outer surface of the insertion portion 5649 being adapted to the concave curved lamella portions 1127 of the retention insert 17, the retention insert 17 is held at the mounting head 569 of the mounting tool 59 essentially without a radial force acting on the retention rim 117 of the retention insert 17 and outwardly moving it or deforming it.

Figure 16:
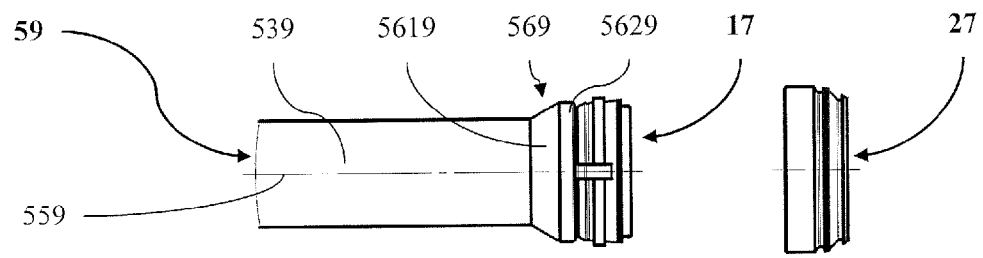
FIG. 16 shows a side view of the section of the mounting tool of FIG. 13 during mounting of the retention insert of the connection device of FIG. 11 before inserting it in the holding shell of the connection device of FIG. 11.
Figure 17:
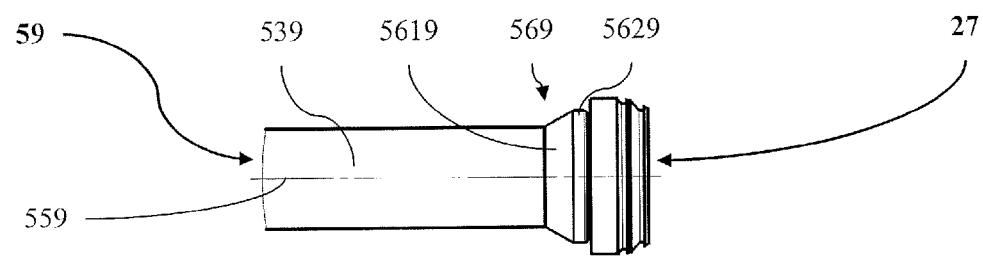
FIG. 17 shows a side view of the section of the mounting tool of FIG. 13 during mounting of the retention insert of the connection device of FIG. 11 after inserting it in the holding shell of the connection device of FIG. 11.
Figure 18:
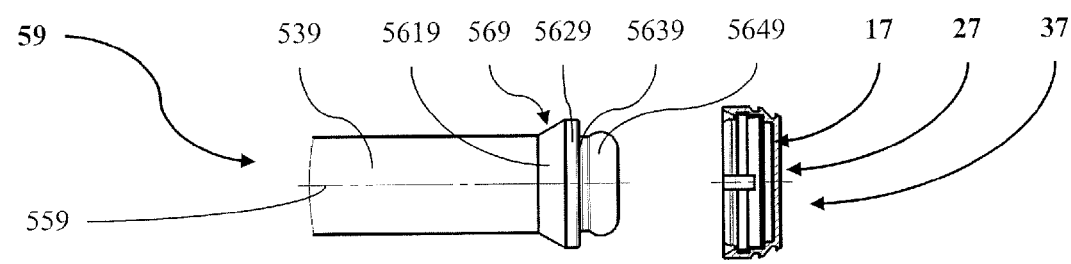
FIG. 18 shows a side view of the section of the mounting tool of FIG. 13 after mounting of the retention insert of the connection device of FIG. 11 to the cross-sectionally shown holding shell of the connection device of FIG. 11.

In the following, the retention insert 17 can be freely moved around and appropriately positioned together with the mounting tool 59. In particular, as shown in FIG. 16, it is arranged axially spaced at the open side of the holding shell 27 of the connection device 37. As shown in FIG. 17, the retention insert 17 is pressed into the holding shell 27 by means of the mounting tool 59. Therein, the projection 137 of the retention insert 17 partially lies inside the groove 237 of the holding shell 27. In this position the retention insert 17 is held on one hand by the lamella portions 1127 of the retention insert 17 interacting with the insertion portion 5649 of the mounting head 569 of the mounting tool 59 and on the other hand by the projection 137 of the retention insert 17 partially lying in the groove 237 of the holding shell 27. Thereby, a holding force between the holding shell 27 and the retention insert 17 is bigger than a holding force between the mounting tool 59 and the retention insert 17. Thus, as shown in FIG. 18, the mounting tool 59 can conveniently be pulled out of the retention insert 17 wherein the retention insert 17 remains in the holding shell 27. In this position, the retention insert 17 is mounted to the holding shell 27.

Figure 19:
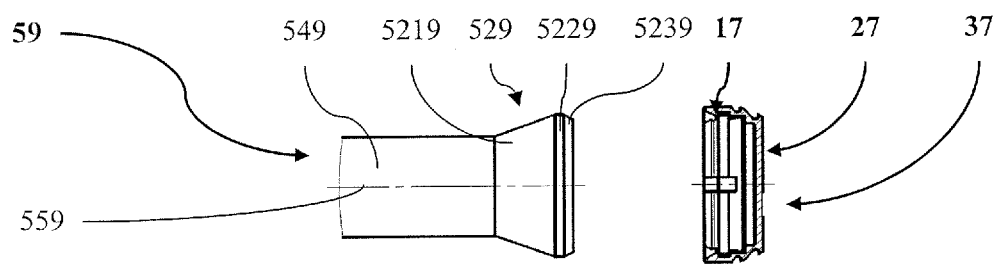
FIG. 19 shows a side view of a further section of the mounting tool of FIG. 13 during demounting of the retention insert of the connection device of FIG. 11 from the cross-sectionally shown holding shell of the connection device of FIG. 11 before accommodating it.
Figure 20:
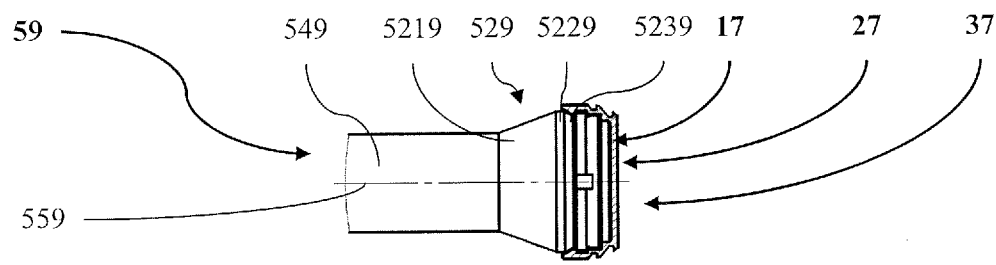
FIG. 20 shows a side view of the further section of the mounting tool of FIG. 13 during demounting of the retention insert of the connection device of FIG. 11 from the cross-sectionally shown holding shell of the connection device of FIG. 11 after accommodating it.
Figure 21:
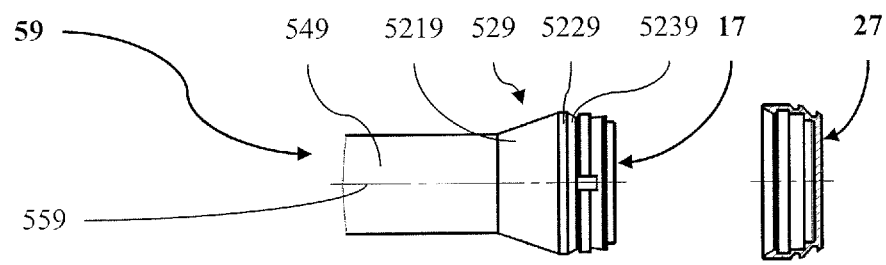
FIG. 21 shows a side view of the further section of the mounting tool of FIG. 13 after demounting of the retention insert of the connection device of FIG. 11 from the cross-sectionally shown holding shell of the connection device of FIG. 11.

As shown in FIG. 19, for demounting the retention insert 17, the mounting tool 59 is arranged with its demounting head 529 facing the open side of the retention insert 17 and axially spaced therefrom. Afterwards, as shown in FIG. 20, the engagement portion 5239 as well as partially also the intermediate portion 5229 of the demounting head 529 are pressed between the holding rim 217 of the holding shell 27 and the retention rim 117 of the retention insert 17. Thereby, the engagement portion 5239 engages into the engagement groove 1157 of the retention rim 117 such that the retention insert is held at the mounting tool 59. In this position, the retention insert 17 is held on one hand by the projection 137 of the retention insert 17 partially lying in the groove 237 of the holding shell 27 and on the other hand by the engagement portion 5239 engaging into the engagement groove 1157. Thereby, a holding force between the holding shell 27 and the retention insert 17 is smaller than a holding force between the mounting tool 59 and the retention insert 17. Thus, as shown in FIG. 21, the mounting tool 59 together with the retention insert 17 can conveniently be pulled out of the holding shell 27. In this position, the retention insert 17 is demounted from the holding shell 27.

Although the invention is illustrated and described in detail on the basis of the Figures and the corresponding description, this illustration and this detailed description are to be understood to be illustrative and exemplary and not as restricting the invention. It is self-evident that experts can make changes and adaptations without leaving the scope and the gist of the following claims. In particular, the invention also comprises embodiments with any combination of features which are mentioned or shown above or below in connection with different embodiments.

The invention also comprises individual features in the Figures, even if they are shown therein in connection with other features and/or if they are not mentioned above or below. The embodiments described in the Figures and the description and individual features thereof can also be excluded from the subject-matter of the invention.

Moreover, the term "comprise" and derivations thereof do not exclude other elements or steps. Furthermore, the indefinite article "a" and derivations thereof do not exclude a plurality. The functions of several of the features mentioned in the claims can be fulfilled by a unity. The terms "substantially", "about", "approximately" and the like in connection with a characteristic or a value in particular also define exactly this characteristic or exactly this value. All reference signs in the claims are not to be understood as restricting the scope of the claims.

The invention claimed is:

1. A connection device (3: 37) for connecting a prosthesis structure with an implant structure or capped tooth, both having a head suitable for a snap engagement connection, said connection device comprising;
    a holding shell (2; 27) and a retention insert (1, 17; 18; 19),
    wherein said retention insert (1; 17; 18; 19) has an end side (12; 127; 128; 129) and a substantially ring shaped retention rim (11; 117; 118; 119) projecting therefrom;
    wherein said holding shell (2; 27) has an end side (22; 227) and a substantially ring shaped holding rim (21; 217) projecting therefrom;
    wherein said holding rim (21; 217) and said end side (22; 227) of said holding shell (2; 27) form a retainer in which said retention insert (1; 17; 18; 19) can be arranged such that an outer surface (114; 1147; 1148; 1149) of said retention rim (11; 117; 118; 119) of said retention insert (1; 17; 18; 19) is adjacent to an inner surface (212; 2127) of said holding rim (21; 217) of said holding shell (2; 27);
    wherein said retention rim (11; 117; 118; 119) of said retention insert (1; 17; 18; 19) has a projection (13; 137; 138; 139) projecting radially from said outer surface (114; 1147; 1148; 1149) of said retention rim (11; 117; 118; 119) of said retention insert (1; 17; 18; 19) and said holding rim (21; 217) of said holding shell (2; 27) comprises a corresponding groove (23; 237) extending radially from said inner surface (212; 2127) of said holding rim (21; 217) of said holding shell (2; 27);
    wherein said projection (13; 137; 138; 139) of said retention rim (11; 117; 118; 119) of said retention insert (1; 17; 18; 19) is arrangeable in said groove (23; 237) of said holding rim (21; 217) of said holding shell (2; 27) and said outer surface (114; 1147; 1148; 1149) of said retention rim (11; 117; 118; 119) of said retention insert (1; 17; 18; 19) is at least partly spaced from and adjacent to said inner surface (212; 2127) of said holding rim (21; 217) of said holding shell (21; 217), such that said retention insert (1; 17; 18; 19) is releasably held in said retainer of said holding shell (2; 27), defining a first position where said head is not inserted in the retention insert and the retention insert is removable from said holding shell; and
    wherein said retention insert (1; 17; 18; 19) is radially expandable by a radial force acting on said retention rim (11; 117; 118; 119) in the direction of said holding rim (21; 217) of said holding shell (2; 27) by insertion of said head into said retention insert, defining a second position, wherein in said second position, said projection of said retention rim of said retention insert is moved further into and in the direction of said groove of said holding rim of said holding shell and spacing between said retention rim of said retention insert and said inner surface of said holding rim of said holding shell is reduced, and the retention insert is firmly held in and is not removable from said holding shell.

2. The connection device (3; 37) according to claim 1, wherein said outer surface (114; 1147; 1148; 1149) of said retention rim (11; 117; 118; 119) of said retention insert (1; 17; 18; 19) is at least partly spaced from and adjacent to said inner surface (212; 2127) of said holding rim (21; 217) of said holding shell (2; 27) in that an angle between said outer surface (114; 1147; 1148; 1149) of said retention rim (11; 117; 118; 119) of said retention insert (1; 17; 18; 19) and a central axis (15, 25; 157, 257) of said connection device (3; 37) is smaller than an angle between said inner surface (212; 2127) of said holding rim (21; 217) of said holding shell (2; 27) and said central axis (15, 25; 157, 257) of said connection device (3; 37).

3. The connection device (3; 37) according to claim 1, wherein said retention rim (11; 117; 118; 119) of said retention insert (1; 17; 18; 19) comprises recesses (111; 1117; 1118; 1119) starting from an end of said retention rim (11; 117; 118; 119) extending away from said end side (12; 127; 128; 129) of said retention insert (1; 17; 18; 19) and extending in the direction of said end side (12; 127; 128; 129) of said retention insert (1; 17; 18; 19).

4. The connection device (3; 37) according to claim 3, wherein said recesses (111; 1117; 1118; 1119) in said retention rim (11; 117; 118; 119) of said retention insert (1; 17; 18; 19) extend along over at least about 50% of said retention rim (11; 117; 118; 119) of said retention insert (1; 17; 18; 19), preferably over at least about 70% of said retention rim (11; 117; 118; 119) of said retention insert (1; 17; 18; 19) and in particular over at least about 80% of said retention rim (11; 117; 118; 119) of said retention insert (1; 17; 18; 19).

5. The connection device (3; 37) according to claim 3, wherein said retention rim (11; 117; 118; 119) of said retention insert (1; 17; 18; 19) comprises three, four, five or six recesses (111; 1117; 1118; 1119).

6. The connection device (3; 37) according to claim 1, wherein said projection (13; 137; 138; 139) of said retention rim (11; 117; 118; 119) of said retention insert (1; 17; 18; 19) comprises a substantially planar projection supporting surface (131; 1317; 1318; 1319) and said groove (23; 237) of said holding rim (21; 217) of said holding shell (2; 27) comprises a substantially planar groove supporting surface (231; 2317), wherein a part of said projection supporting surface (131; 1317; 1318; 1319) contacts a part of said groove supporting surface (231; 2317) when said retention insert (1; 17; 18; 19) is arranged in the retainer of said holding shell (2; 27) in said first position, and wherein said groove supporting surface (231; 2317) is rounded towards its end facing said retention insert (1; 17; 18; 19) and/or said projection supporting surface (131; 1317; 1318; 1319) is rounded towards its end facing said holding shell (2; 27).

7. The connection device (3; 37) according claim 1, wherein said retention rim (11; 117; 118; 119) of said retention insert (1; 17; 18; 19) comprises an inner surface (112, 113; 1127, 1137; 1128, 1138; 1129, 1139) opposite to said outer surface (114; 1147; 1148; 1149), wherein said inner surface (112, 113; 1127, 1137; 1128, 1138; 1129, 1139) is rounded towards an end facing away from the end side (12; 127; 128; 129) of said retention insert (1; 17; 18; 19).

8. The connection device (3; 37) according to claim 1, wherein said retention insert (1; 17; 18; 19) and/or said holding shell (2; 27) is/are made of a biocompatible polymeric material, in particular of a polyetheretherketone.

9. The connection device (3; 37) according to claim 1, wherein an engagement groove (1157) is formed on said outer surface (114; 1147; 1148; 1149) of said retention rim (11; 117; 118; 119) of said retention insert (1; 17; 18; 19), which preferably extends over the entire circumference of said retention rim (11; 117; 118; 119) of said retention insert (1; 17; 18; 19).

10. A method for connecting a prosthesis structure with an implant structure by means of a connection device (3; 37) according to claim 1, wherein said holding shell (2; 27) of said connection device (3; 37) is firmly mounted to the prosthesis structure and wherein the implant structure comprises said head suitable for a snap-engagement connection, comprising the steps of inserting said retention insert (1; 17; 18; 19) of said connection device (3; 37) axially into said holding shell (2; 27) of the connection device (3; 37) until said retention insert (1; 17; 18; 19) is arranged in said holding shell (2; 27), in said first position arranging the prosthesis structure at the implant structure so that the head of the implant structure contacts said retention insert (1; 17; 18; 19) of said connection device (3; 37), and pressing the prosthesis structure on the implant structure so that said retention insert (1; 17; 18; 19) is pressed axially on the head of the implant structure, such that said retention insert is moved from said first position to said second position.

* * * * *